(12) United States Patent
Olsen et al.

(10) Patent No.: US 8,849,417 B2
(45) Date of Patent: *Sep. 30, 2014

(54) LEAD ELECTRODE FOR USE IN AN MRI-SAFE IMPLANTABLE MEDICAL DEVICE

(75) Inventors: James M. Olsen, Plymouth, MN (US); Gregory A. Hrdlicka, Plymouth, MN (US); Carl D. Wahlstrand, Lino Lakes, MN (US); Thomas Barry Hoegh, Edina, MN (US)

(73) Assignee: Medtronic, Inc., Minneapolis, MN (US)

( * ) Notice: Subject to any disclaimer, the term of this patent is extended or adjusted under 35 U.S.C. 154(b) by 980 days.

This patent is subject to a terminal disclaimer.

(21) Appl. No.: 12/954,585

(22) Filed: Nov. 24, 2010

(65) Prior Publication Data

US 2011/0071599 A1    Mar. 24, 2011

Related U.S. Application Data

(63) Continuation of application No. 11/117,882, filed on Apr. 29, 2005, now Pat. No. 7,853,332.

(51) Int. Cl.
*A61N 1/05* (2006.01)
*A61N 1/08* (2006.01)

(52) U.S. Cl.
CPC ............ *A61N 1/0529* (2013.01); *A61N 1/0553* (2013.01); *A61N 2001/086* (2013.01)
USPC ............................................ 607/116; 607/63

(58) Field of Classification Search
USPC .................... 600/373–394; 607/115–130, 63
See application file for complete search history.

(56) References Cited

U.S. PATENT DOCUMENTS 5,370,644 A * 12/1994 Langberg .................... 606/33
2003/0083726 A1 * 5/2003 Zeijlemaker et al. ......... 607/122

* cited by examiner

*Primary Examiner* — Scott Getzow (57) ABSTRACT

A medical lead is configured to be implanted into a patient's body and comprises a lead body, and an electrode coupled to the lead body. The electrode comprises a first section configured to contact the patient's body, and a second section capacitively coupled to the first section and configured to be electrically coupled to the patient's body.

23 Claims, 9 Drawing Sheets

LEAD ELECTRODE FOR USE IN AN MRI-SAFE IMPLANTABLE MEDICAL DEVICE

RELATED APPLICATIONS

The present application is a continuation of U.S. patent application Ser. No. 11/117,882, filed on Apr. 29, 2005 now U.S. Pat. No. 7,853,332, and entitled LEAD ELECTRODE FOR USE IN AN MRI-SAFE IMPLANTABLE MEDICAL DEVICE, which is incorporated by reference herein.

FIELD OF THE INVENTION

The present invention generally relates to implantable medical devices, and more particularly to an implantable MRI-safe lead of the type which includes a stimulation electrode for use in conjunction with an implantable medical device such as a neurostimulation system that when used in an MRI environment conveys energy induced at MRI frequencies to a patient's body in a safe manner.

BACKGROUND OF THE INVENTION

Implantable medical devices are commonly used today to treat patients suffering from various ailments. Such implantable devices may be utilized to treat conditions such as pain, incontinence, sleep disorders, and movement disorders such as Parkinson's disease and epilepsy. Such therapies also appear promising in the treatment of a variety of psychological, emotional, and other physiological conditions.

One known type of implantable medical device, a neurostimulator, delivers mild electrical impulses to neural tissue using an electrical lead. For example, to treat pain, electrical impulses may be directed to specific sites. Such neurostimulation may result in effective pain relief and a reduction in the use of pain medications and/or repeat surgeries.

Typically, such devices are totally implantable and may be controlled by a physician or a patient through the use of an external programmer. Current systems generally include a non-rechargeable primary cell neurostimulator, a lead extension, and a stimulation lead, and the two main classes of systems may be referred to as: (1) Spinal Cord Stimulation (SCS) and (2) Deep Brain Stimulation (DBS).

An SCS stimulator may be implanted in the abdomen, upper buttock, or pectoral region of a patient and may include at least one extension running from the neurostimulator to the lead or leads which are placed somewhere along the spinal cord. Each of the leads (to be discussed in detail hereinbelow) currently contains from one to eight electrodes. Each extension (likewise to be discussed in detail below) is plugged into or connected to the neurostimulator at a proximal end thereof and is coupled to and interfaces with the lead or leads at a distal end of the extension.

The implanted neurostimulation system is configured to send mild electrical pulses to the Spinal cord. These electrical pulses are delivered through the lead or leads to regions near the spinal cord or a nerve selected for stimulation. Each lead includes a small insulated wire coupled to an electrode at the distal end thereof through which the electrical stimulation is delivered. Typically, the lead also comprises a corresponding number of internal wires to provide separate electrical connection to each electrode such that each electrode may be selectively used to provide stimulation. Connection of the lead to an extension may be accomplished by means of a connector block including, for example, a series or combination of set screws, ball seals, etc. The leads are inserted into metal set screw bocks, and the metal set screws are manipulated to press the contacts against the blocks to clamp them in place and provide electrical connection between the lead wires and the blocks. Such an arrangement is shown in U.S. Pat. No. 5,458,629 issued Oct. 17, 1995 and entitled "Implantable Lead Ring Electrode and Method of Making".

A DBS system comprises similar components (i.e. a neurostimulator, at least one extension, and at least one stimulation lead) and may be utilized to provide a variety of different types of electrical stimulation to reduce the occurrence or effects of Parkinson's disease, epileptic seizures, or other undesirable neurological events. In this case, the neurostimulator may be implanted into the pectoral region of the patient. The extension or extensions may extend up through the patient's neck, and the leads/electrodes are implanted in the brain. The leads may interface with the extension just above the ear on both sides of the patient. The distal end of the lead may contain from four to eight electrodes and, as was the case previously, the proximal end of the lead may be connected to the distal end of the extension and may be held in place by set screws. The proximal portion of the extension plugs into the connector block of the neurostimulator.

Magnetic resonance imaging (MRI) is a relatively new and efficient technique that may be used in the diagnosis of many neurological disorders. It is an anatomical imaging tool which utilizes non-ionizing radiation (i.e. no x-rays or gamma rays) and provides a non-invasive method for the examination of internal structure and function. For example, MRI permits the study of the overall function of the heart in three dimensions significantly better than any other imaging method. Furthermore, imaging with tagging permits the non-invasive study of regional ventricular function.

MRI scanning is widely used in the diagnosis of injuries to the head. In fact, the MRI is now considered by many to be the preferred standard of care, and failure to prescribe MRI scanning can be considered questionable. Approximately sixteen million MRIs were performed in 1996, followed by approximately twenty million in the year 2000. It is projected that forty million MRIs will be performed in 2004.

In an MRI scanner, a magnet creates a strong magnetic field which aligns the protons of hydrogen atoms in the body and then exposes them to radio frequency (RF) energy from a transmitter portion of the scanner. This spins the various protons, and they produce a faint signal that is detected by a receiver portion of the scanner. A computer renders these signals into an image. During this process, three electromagnetic fields are produced; i.e. (1) a static magnetic field, (2) a gradient magnetic field, and (3) a radio frequency (RF) magnetic field. The main or static magnetic field may typically vary between 0.2 and 3.0 Tesla. A nominal value of 1.5 Tesla is approximately equal to 15,000 Gauss which is 30,000 times greater than the Earth's magnetic field of approximately 0.5 Gauss. The time varying or gradient magnetic field may have a maximum strength of approximately 40 milli-Tesla/meters at a frequency of 0-5 KHz. The RF may, for example, produce thousands of watts at frequencies of between 8-215 MHz. For example, up to 20,000 watts may be produced at 64 MHz and a static magnetic field of 1.5 Tesla; that is, 20 times more power than a typical toaster. Thus, questions have arisen regarding the potential risk associated with undesirable interaction between the MRI environment and the above-described neurostimulation systems; e.g. forces and torque on the implantable device within the MRI scanner caused by the static magnetic field, RF-induced heating, induced currents due to gradient magnetic fields, device damage, and image distortion. Of these interactions, the problems associated with induced RF currents in the leads are most deserving of attention since it has been found that the temperature in the leads can rise by as much as 25° Centigrade or higher in an MRI environment.

A similar problem occurs when a patient undergoes diathermy treatment employing RF energy to create eddy currents in the patient's tissue so as to heat the tissue and promote healing. In this environment, current may also be produced in the implanted lead causing undesirable heating of the electrodes as described above.

Accordingly, it would be desirable to provide an implantable medical device that may be safely operated in an MRI environment. It would be further desirable to provide an implantable medical device such as a SCS or DBS neurostimulation system that may be operated in an MRI environment without the generation of significant undesirable heat in the leads due to induced RF currents. It would be further desirable to provide an MRI-safe, implantable lead that may be used in conjunction with known implantable medical devices wherein the stimulation electrodes shunt the energy induced in the electrodes during an MRI scan safely to a patient's body, thereby reducing the generation of unwanted heat at the leads stimulation electrodes. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

According to an aspect of the invention there is provided a medical electrode assembly for use on a lead configured to be implanted in a patient's body. The electrode comprises a first section configured to contact the patient's body, and a second section capacitively coupled to the first section and configured to be electrically coupled to the patient's body.

According to a still further aspect of the present invention there is provided a pulse stimulation system for implantation into a patient's body. The system comprises a pulse generator, a conductive filer having a proximal end electrically coupled to the pulse generator and having a distal end, a lead body for housing the conductive filer, and a stimulation electrode configured on the lead body and electrically coupled to the distal end of the filer. The stimulation electrode comprises a first section configured to contact the patient's body for delivering stimulation thereto, and a second section electrically coupled to the first section and configured to be capacitively coupled to the patient's body.

BRIEF DESCRIPTION OF THE DRAWINGS

The present invention will hereinafter be described in conjunction with the following drawing figures, wherein like numerals denote like elements, and.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
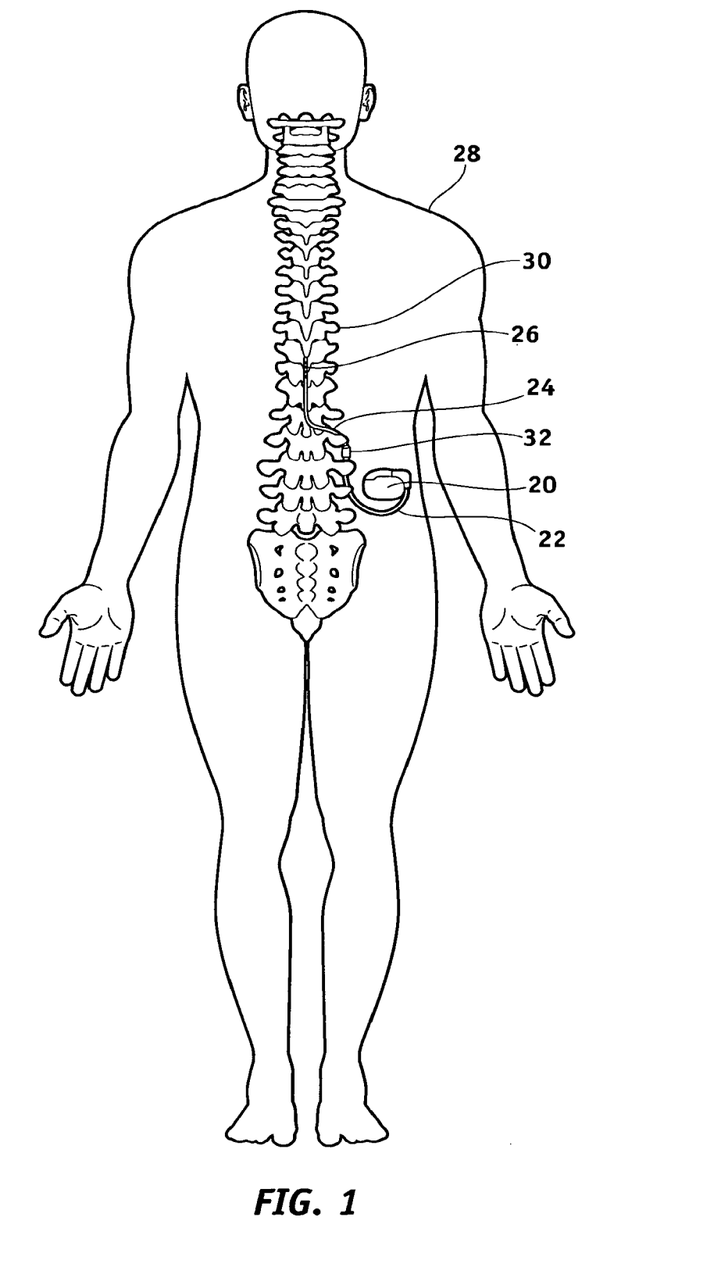
FIG. 1 illustrates a typical spinal cord stimulation system implanted in a patient.

FIG. 1 illustrates a typical SCS system implanted in a patient. As can be seen, the system comprises a pulse generator such as an SCS neurostimulator 20, a lead extension 22 having a proximal end coupled to neurostimulator 20 as will be more fully described below, and a lead 24 having proximal end coupled to the distal end of extension 22 and having a distal end coupled to one or more electrodes 26. Neurostimulator 20 is typically placed in the abdomen of a patient 28, and lead 24 is placed somewhere along spinal cord 30. As stated previously, neurostimulator 20 may have one or two leads each having four to eight electrodes. Such a system may also include a physician programmer and a patient programmer (not shown). Neurostimulator 20 may be considered to be an implantable pulse generator of the type available from Medtronic, Inc. and capable of generating multiple pulses occurring either simultaneously or one pulse shifting in time with respect to the other, and having independently varying amplitudes and pulse widths. Neurostimulator 20 contains a power source and the electronics for sending precise, electrical pulses to the spinal cord to provide the desired treatment therapy. While neurostimulator 20 typically provides electrical stimulation by way of pulses, other forms of stimulation may be used as continuous electrical stimulation.

Lead 24 is a small medical wire having special insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available form Medtronic, Inc.). Lead 24 may contain a paddle at its distant end for housing electrodes 26; e.g. a Medtronic paddle having model number 3587A. Alternatively, electrodes 26 may comprise one or more ring contacts at the distal end of lead 24 as will be more fully described below.

While lead 24 is shown as being implanted in position to stimulate a specific site in spinal cord 30, it could also be positioned along the peripheral nerve or adjacent neural tissue ganglia or may be positioned to stimulate muscle tissue. Furthermore, electrodes 26 may be epidural, intrathecal or placed into spinal cord 30 itself. Effective spinal cord stimulation may be achieved by any of these lead placements. While the lead connector at proximal end of lead 24 may be coupled directly to neurostimulator 20, the lead connector is typically coupled to lead extension 22 as is shown in FIG. 1. An example of a lead extension is Model 7495 available from Medtronic, Inc.

A physician's programmer (not shown) utilizes telemetry to communicate with the implanted neurostimulator 20 to enable the physician to program and manage a patient's therapy and troubleshoot the system. A typical physician's programmer is available from Medtronic, Inc. and bears Model No. 7432. Similarly, a patient's programmer (also not shown) also uses telemetry to communicate with neurostimulator 20 so as to enable the patient to manage some aspects of their own therapy as defined by the physician. An example of a patient programmer is Model 7434® 3 EZ Patient Programmer available from Medtronic, Inc.

Implantation of a neurostimulator typically begins with the implantation of at least one stimulation lead usually while the patient is under a local anesthetic. While there are many spinal cord lead designs utilized with a number of different implantation techniques, the largest distinction between leads revolves around how they are implanted. For example, surgical leads have been shown to be highly effective, but require a laminectomy for implantation. Percutaneous leads can be introduced through a needle, a much easier procedure. To simplify the following explanation, discussion will focus on percutaneous lead designs, although it will be understood by those skilled in the art that the inventive aspects are equally applicable to surgical leads. After the lead is implanted and positioned, the lead's distal end is typically anchored to minimize movement of the lead after implantation. The lead's proximal end is typically configured to connect to a lead extension 22. The proximal end of the lead extension is then connected to the neurostimulator 20.

Figure 2:
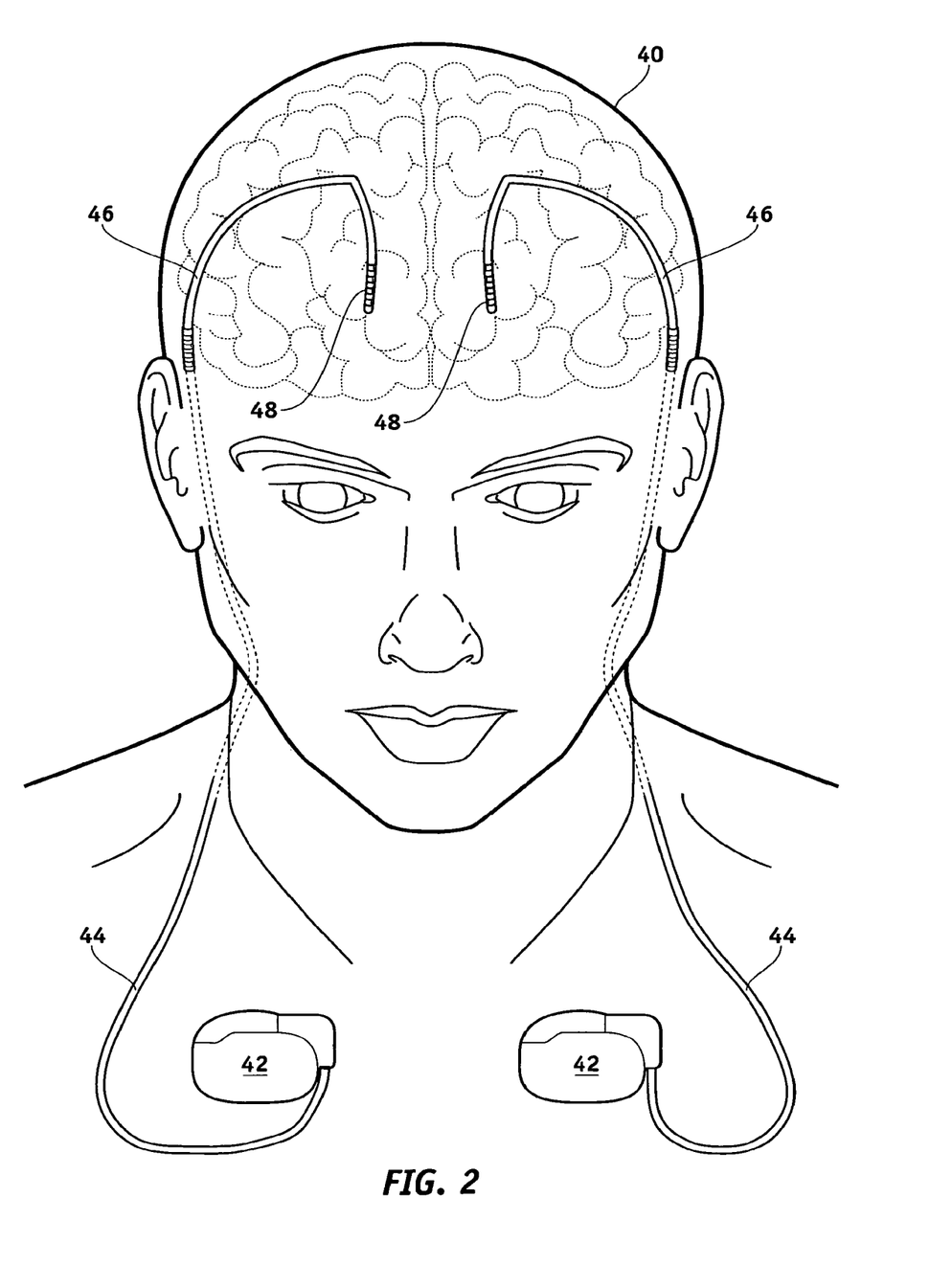
FIG. 2 illustrates a typical deep brain stimulation system implanted in a patient.

FIG. 2 illustrates a DBS system implanted in a patient 40 and comprises substantially the same components as does an SCS; that is, at least one neurostimulator, at least one extension, and at least one stimulation lead containing one or more electrodes. As can be seen, each neurostimulator 42 is implanted in the pectoral region of the patient. Extensions 44 are deployed up through the patient's neck, and leads 46 are implanted in the patient's brain is as shown at 48. As can be seen, each of the leads 46 is connected to its respective extension 44 just above the ear on both sides of patient 40.

Figure 3:
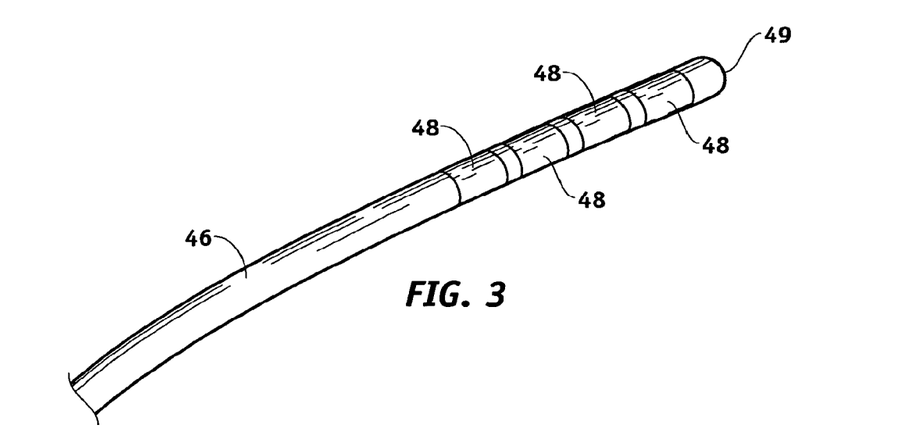
FIG. 3 is an isometric view of the distal end of the lead shown in FIG. 2.
Figure 4:
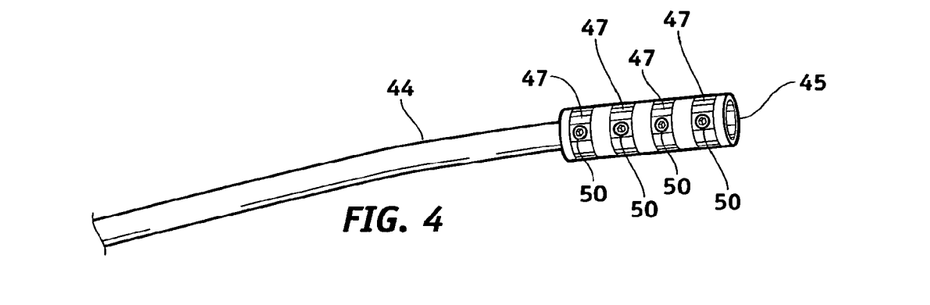
FIG. 4 is an isometric view of the distal end of the extension shown in FIG. 2.
Figure 5:
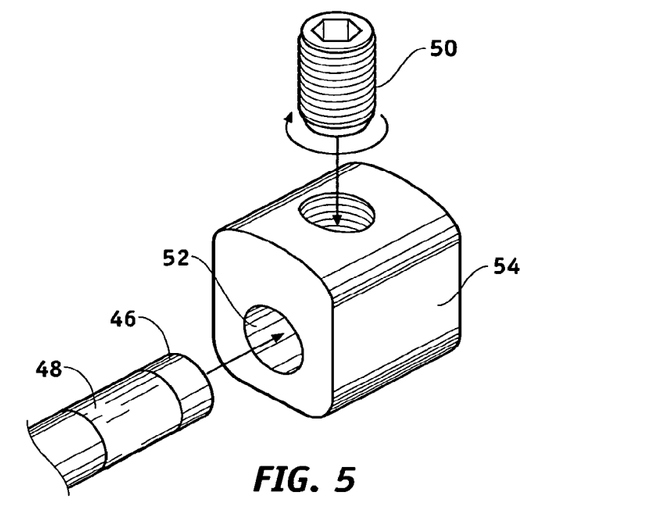
FIG. 5 is an isometric view of an example of a connector screw block suitable for connecting the lead of FIG. 3 to the extension shown in FIG. 4.

FIG. 3 is an isometric view of the distal end of lead 46. In this case, four ring electrodes 48 are positioned on the distal end of lead 46 and coupled to internal conductors of filers (not shown) contained within lead 46. Again, while four ring electrodes are shown in FIG. 3, it is to be understood that the number of electrodes can vary to suit a particular application. FIG. 4 is an isometric view of the distal end of extension 44, which includes a connector portion 45 having four internal contacts 47. The proximal end of the DBS lead is shown in FIG. 3, plugs into the distal connector 45 of extension 44, and is held in place by means of, for example, a plurality (e.g. 4) of set screws 50. For example, referring to FIG. 5, lead 46 terminates in a series of proximal electrical ring contacts 48 (only one of which is shown in FIG. 5). Lead 46 may be inserted through an axially aligned series of openings 52 (again only one shown) in screw block 54. With a lead 46 so inserted, a series of set screws (only one shown) are screwed into block 54 to drive contacts 48 against blocks 54 sand secure and electrically couple the lead 46. It should be appreciated, however, that other suitable methods for securing lead 46 to extension 44 may be employed. The proximal portion of extension 44 is secured to neurostimulator 42 as is shown in FIGS. 1 and 2.

Figure 6:
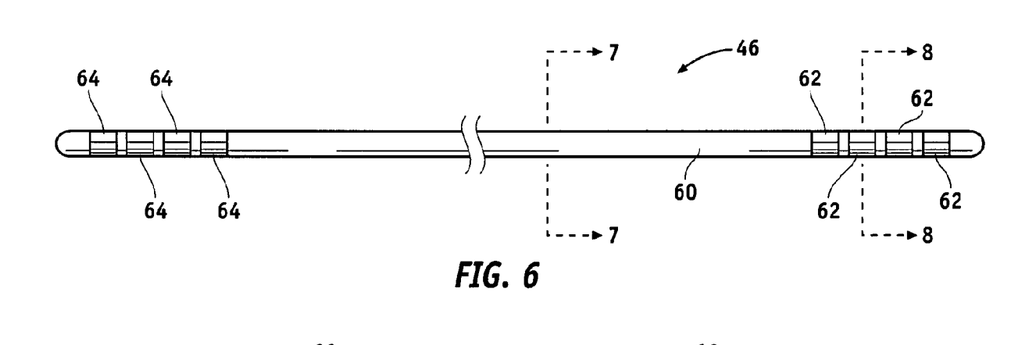
FIG. 6 is a top view of the lead shown in FIG. 2.
Figure 7:
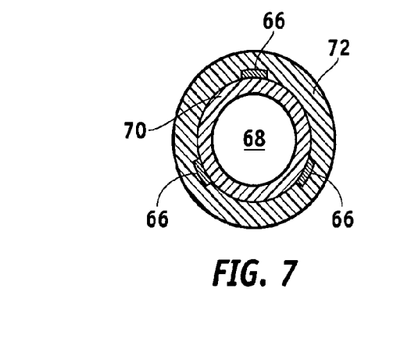
FIGS. 7 and 8 are cross-sectional views taken along lines 7-7 and 8-8, respectively, in FIG. 6.
Figure 8:
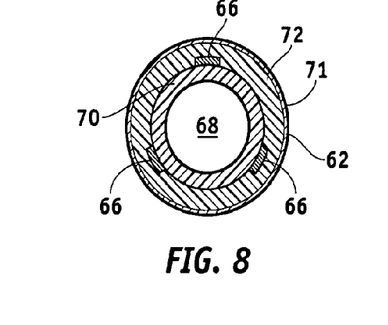

FIG. 6 is a top view of lead 46 shown in FIG. 2. FIGS. 7 and 8 are cross-sectional views taken along lines 7-7 and 8-8, respectively, in FIG. 6. Distal end 60 of lead 46 includes at least one electrode 62 (four are shown). As stated previously, up to eight electrodes may be utilized. Each of electrodes 62 is preferably constructed as is shown in FIG. 8. That is, electrode 62 may comprise a conductive ring 71 on the outer surface of the elongate tubing making up distal shaft 60. Each electrode 62 is electrically coupled to a longitudinal wire 66 (shown in FIGS. 7 and 8) each of which extends to a contact 64 at the proximal end of lead 46. Longitudinal wires 66 may be of a variety of configurations; e.g. discreet wires, printed circuit conductors, etc. From the arrangement shown in FIG. 6, it should be clear that four conductors or filers run through the body of lead 46 to electrically connect the proximal electrodes 64 to the distal electrodes 62. As will be further discussed below, the longitudinal conductors 66 may be spirally configured along the axis of lead 46 until they reach the connector contacts.

The shaft of lead 46 preferably has a lumen 68 extending therethrough for receiving a stylet that adds a measure of rigidity during installation of the lead. The shaft preferably comprises a comparatively stiffer inner tubing member 70 (e.g. a polyamine, polyamide, high density polyethylene, polypropylene, polycarbonate or the like). Polyamide polymers are preferred. The shaft preferably includes a comparatively softer outer tubing member 72; e.g. silicon or other suitable elastomeric polymer. Conductive rings 71 are preferably of a biocompatible metal such as one selected from the noble group of metals, preferably palladium, platinum or gold and their alloys.

Figure 9:
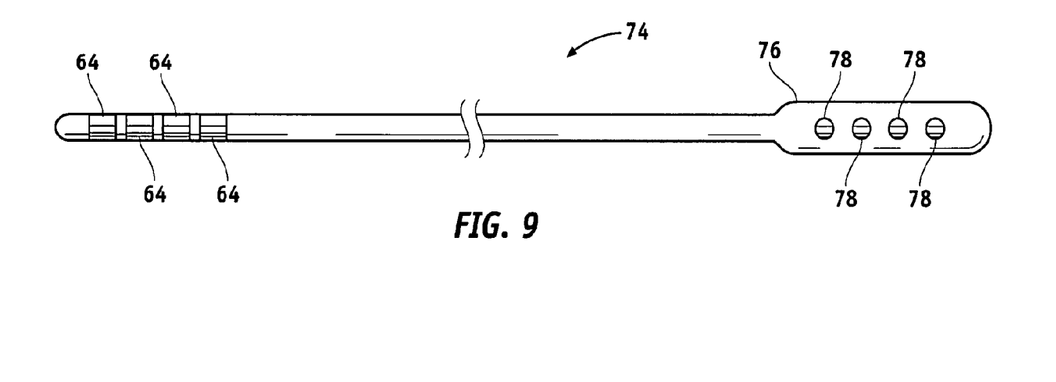
FIG. 9 is a top view of an alternate lead configuration.

FIG. 9 illustrates an alternative lead 74 wherein distal end 76 is broader (e.g. paddle-shaped) to support a plurality of distal electrodes 78. A lead of this type is shown in FIG. 1. As was the case with the lead shown in FIGS. 6,7, and 8, distal electrodes 78 are coupled to contacts 64 each respectively by means of an internal conductor or filer. A more detailed description of the leads shown in FIGS. 6 and 9 may be found in U.S. Pat. No. 6,529,774 issued Mar. 4, 2003 and entitled "Extradural Leads, Neurostimulator Assemblies, and Processes of Using Them for Somatosensory and Brain Stimulation".

Figure 10:
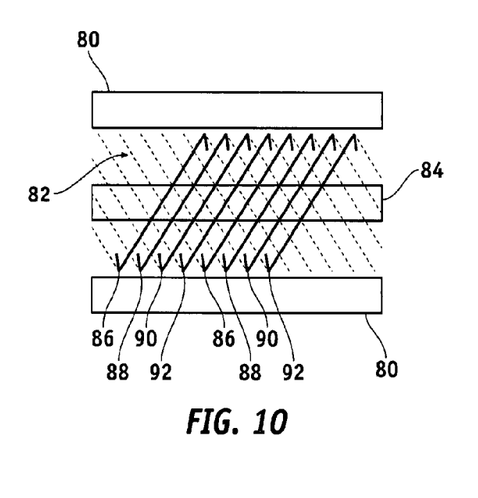
FIGS. 10 and 11 are longitudinal and radial cross-sectional views of a helically wound lead of the type shown in FIG. 6.
Figure 11:
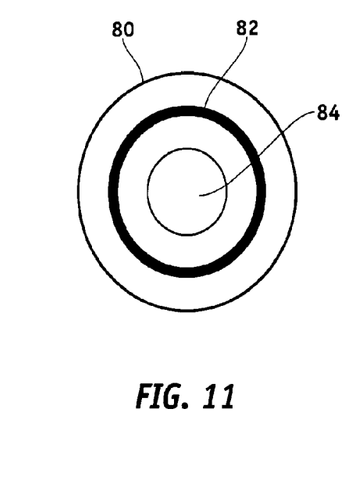

Leads of the type described above may be of the wound helix filer type or of the cabled filer type. FIGS. 10 and 11 are longitudinal and radial cross-sectional views, respectively, of a helically wound lead of the type shown in FIG. 6. The lead comprises an outer lead body 80; a plurality of helically wound, co-radial lead filers 82; and a stylet lumen 84. As stated previously, a stylet is a stiff, formable insert placed in the lead during implant so as to enable the physician to steer the lead to an appropriate location. FIG. 10 illustrates four separate, co-radially wound filers 86, 88, 90, and 92 which are electrically insulated from each other and electrically couple a single electrode 62 (FIG. 6) to a single contact 64 (FIG. 6).

Figure 12:
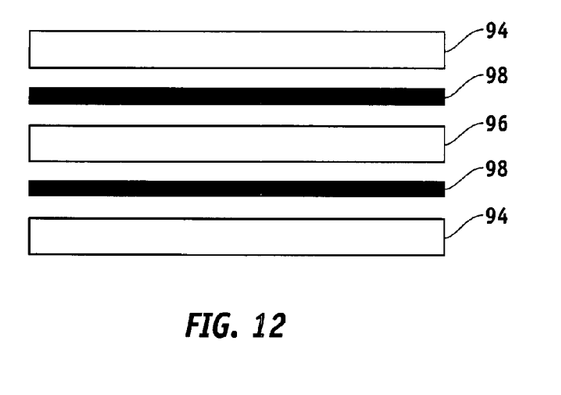
FIGS. 12 and 13 are longitudinal and radial cross-sectional views, respectively, of a cabled lead.
Figure 13:
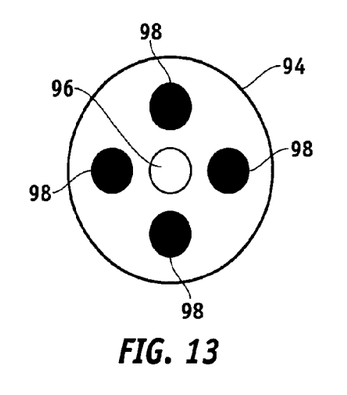

As can be seen, lead filers 82 have a specific pitch and form a helix of a specific diameter. The helix diameter is relevant in determining the inductance of the lead. These filers themselves also have a specific diameter and are made of a specific material. The filer diameter, material, pitch and helix diameter are relevant in determining the impedance of the lead. In the case of a helically wound lead, the inductance contributes to a frequency dependent impedance. FIGS. 12 and 13 are longitudinal and radially cross-sectional views, respectively, of a cabled lead. The lead comprises outer lead body 94, stylet lumen 96, and a plurality (e.g. four to eight) of straight lead filers 98. It should be understood that each straight filer 98 may, if desired, be of a cable construction comprised of a plurality of insulated straight filers; e.g. a center filer surrounded by an additional six filers.

Figures 14, 15:
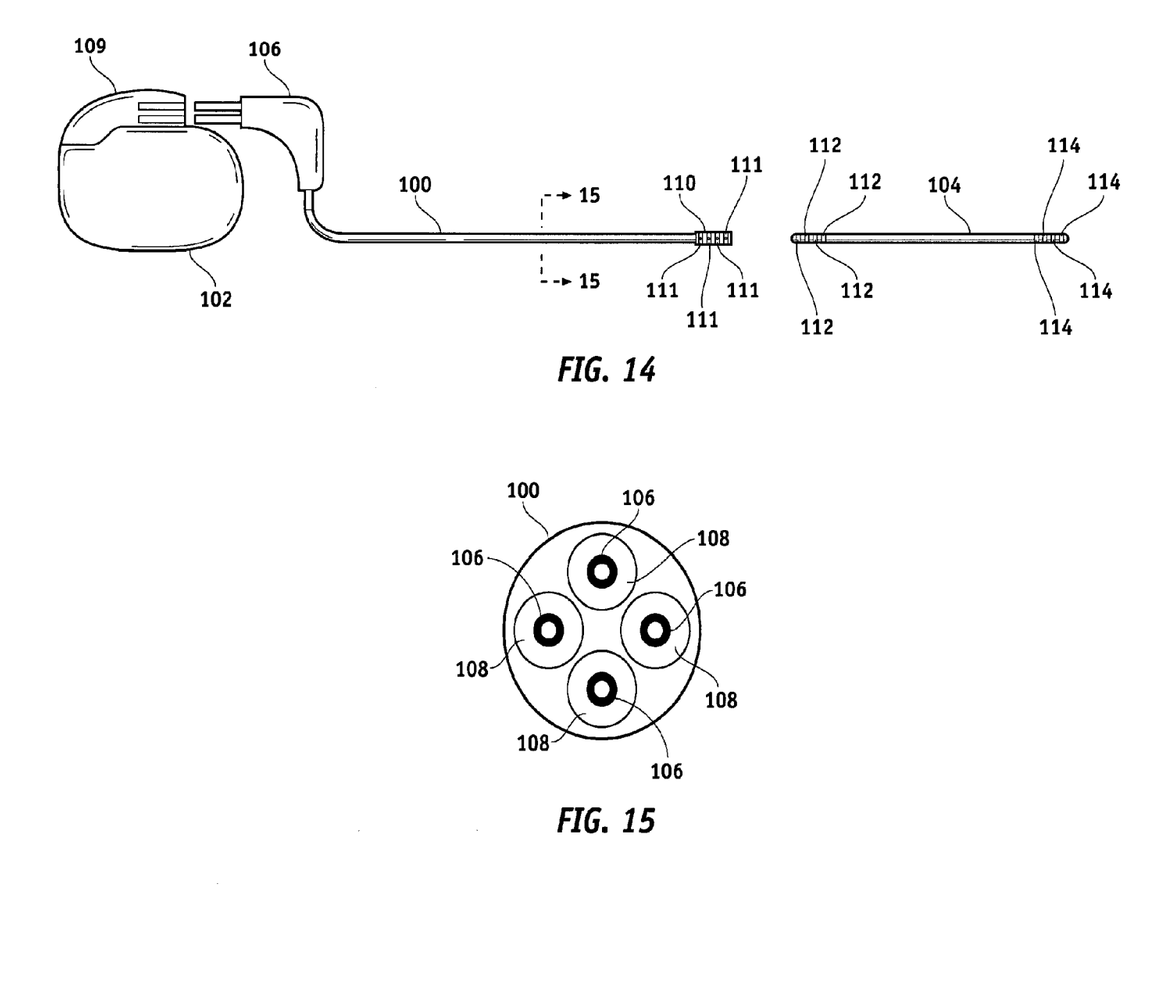
FIG. 14 is an exploded view of a neurostimulation system.
FIG. 15 is a cross-sectional view of the extension shown in FIG. 14 taken along line 15-15.

FIG. 14 is an exploded view of a neurostimulation system that includes an extension 100 configured to be coupled between a neurostimulator 102 and lead 104. The proximal portion of extension 100 comprises a connector 106 configured to be received or plugged into connector block 108 of neurostimulator 102. The distal end of extension 100 likewise comprises a connector 110 including internal contacts 111 and is configured to receive the proximal end of lead 104 having contacts 112 thereon. The distal end of lead 104 includes distal electrodes 114.

FIG. 15 is a cross-sectional view of extension 100. Lead extension 100 has a typical diameter of 0.1 inch, which is significantly larger than that of lead 104 so as to make extension 100 more durable than lead 104. Extension 100 differs from lead 104 also in that each filer 106 in the lead body is helically wound or coiled in its own lumen 108 and not co-radially wound with the rest of the filers as was the case in lead 104.

The diameter of typical percutaneous leads is approximately 0.05 inch. This diameter is based upon the diameter of the needle utilized in the surgical procedure to deploy the lead and upon other clinical anatomical requirements. The length of such percutaneous SCS leads is based upon other clinical anatomical requirements and is typically 28 centimeters; however, other lengths are utilized to meet particular needs of specific patients and to accommodate special implant locations.

Lead length is an important factor in determining the suitability of using the lead in an MRI environment. For example, the greater length of the lead, the larger the effective loop area that is impacted by the electromagnetic field (e.g. the longer the lead, the larger the antenna). Furthermore, depending on the lead length, there can be standing wave effects that create areas of high current along the lead body. This can be problematic if the areas of high current are near the distal electrodes.

Compared to the helically wound lead, the cable lead has smaller DC resistance because the length of the straight filer is less than that of a coiled filer and the impedance at frequency is reduced because the inductance has been significantly reduced. It has been determined that the newer cabled filer designs tend to be more problematic in an MRI environment than do the wound helix filer designs. It should be noted that straight filers for cable leads sometimes comprise braided stranded wire that includes a number of smaller strands woven to make up each filer. This being the case, the number of strands could be varied to alter the impedance.

As stated previously, the electromagnetic fields within an MRI environment produce RF currents in the leads that can result in undesirable temperature increases at the leads stimulation electrodes. It has been discovered that this temperature increase can be reduced by providing stimulation electrodes having effective surface areas that increase in an MRI environment.

Figure 16:
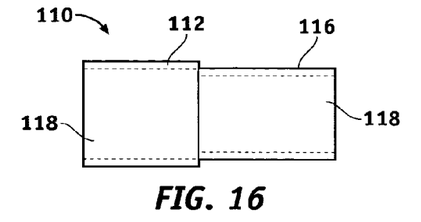
FIGS. 16, 17, and 18 are front, end, and isometric views, respectively, of an electrode in accordance with the present invention.
Figure 17:
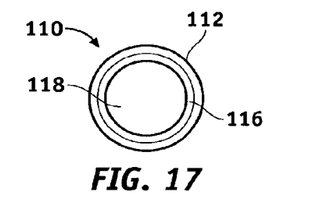
Figure 18:
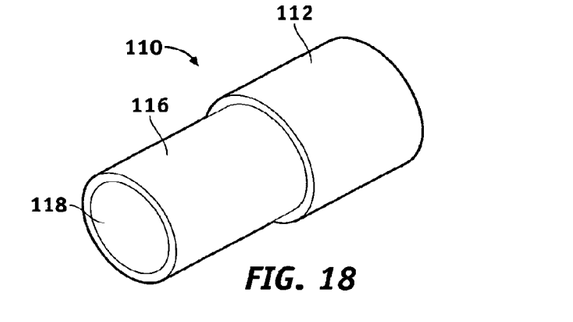
Figure 19:
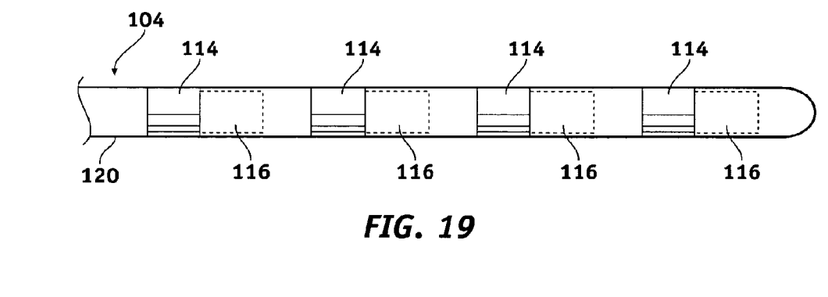
FIG. 19 is a side view of the distal end of a stimulation lead incorporating the electrode shown in FIGS. 16, 17, and 18.

FIGS. 16, 17, and 18 are front, end, and isometric views of a stimulation electrode 110 for use in an MRI-safe stimulation lead. The stimulation electrode comprises a first ring portion 112 having a predetermined outer diameter substantially equal to the outer diameter of lead body 104 (FIG. 19). A second ring portion 116 extends from portion 112 and has an outer diameter smaller than that of the first ring portion. Opening 118 extends through both ring portions to permit conductive filers (not shown) to pass there through.

FIG. 19 is a side view of the distal end of a stimulation lead 104 that has positioned thereon four electrodes 110 of the type previously described in connection with FIGS. 16, 17, and 18. As can be seen, lead 104 includes a lead body 120 having an outer diameter substantially equal to that of the first ring portion 112, and these first ring portions serve as the stimulation electrodes 114 in FIG. 14.

Because second ring portions 116 have a smaller outer diameter, they are covered by lead body 120; i.e. the surface of the second ring portions 116 is covered by a layer of the dielectric lead body material. Thus, the second ring portions are shown in dotted line format in FIG. 19. Alternatively, the electrode may be manufactured with a dielectric layer over the outer surface of the second ring portion. Preferably, the outer diameter of the dielectric layer would have an outer diameter substantially equal to the outer diameter of lead body 120.

During an MRI scan, energy is created in the stimulation lead, and some of that energy exits the lead through the stimulation electrodes in the form of current. This current in the stimulation electrodes can cause the temperature of the electrodes to increase to an undesirable level. By increasing the surface area of the stimulation electrodes, the current density in the stimulation electrodes is decreased thereby decreasing the temperature of the electrodes. By utilizing the second ring portion 116, the stimulation electrode has been effectively extended to be longer than just the stimulation portion of the electrode. The extended portion has a smaller diameter and is covered by a thin layer of dielectric material as above described. When lead 104 is implanted in a patient's body, the second ring portion 116 and the dielectric material thereon form a capacitor with body tissue and/or fluids. The resulting capacitor becomes conductive at MRI frequencies. Thus, at MRI frequencies, the stimulation electrodes have an effective surface area larger than the surface area of their respective first ring portions 112 and the resulting lower density current may be safely dissipated into body tissue or fluid.

The material used to cover the second ring portion 116 may be any type of a biocompatible, non-conductive polymer; preferably a silicone or Teflon type of polymer as these are widely used as lead jackets. The thickness of the layer (i.e. the difference between the outer radii of the first and second ring portions) may be adjusted to select the frequency at which the second ring portion conducts.

Figure 20:
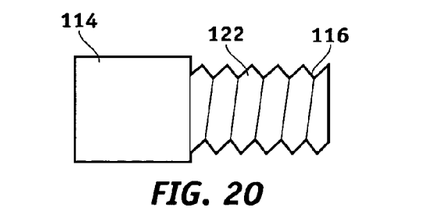
FIG. 20 is a side view of a further embodiment of an electrode in accordance with the present invention.

It is an important design consideration that the lead's handling characteristics are not compromised. For example, a lead equipped with the longer stimulation electrodes shown in FIGS. 16-18 should not be less flexible than previously used leads. To this end, the second ring portion 116 can be flexible and therefore not significantly increase the stiffness of the distal end of the lead. For example, second portion 116 may be in the form of a coil as shown in FIG. 20. Alternatively, second portion 116 may be configured as a braid, fenestrated tube, or bellows.

In another embodiment, heat generated at MRI frequencies can be dissipated by means of a shunt and a floating electrode. Such as arrangement is shown generally in FIG. 21 which is similar to the lead shown in FIG. 14 where like elements are denoted by line reference numerals. That is, lead 104 has a plurality of proximal contacts 112 and a plurality of stimulation electrodes 114. However, the lead shown in FIG. 21 also comprises a floating electrode 124 that is placed somewhere along the length of lead 104, preferably proximate the stimulation electrodes 114. Floating electrode 124 is not used for stimulation but is configured to be capacitively coupled to the stimulation electrodes 114 so as to increase the effective surface area of the electrodes in the high frequency environment of an MRI scan. It should be noted that, if desired, floating electrode 124 may have a layer of dielectric material disposed thereon and thereby be capacitively coupled to the patient's body.

Figures 21, 22, 23, 24:
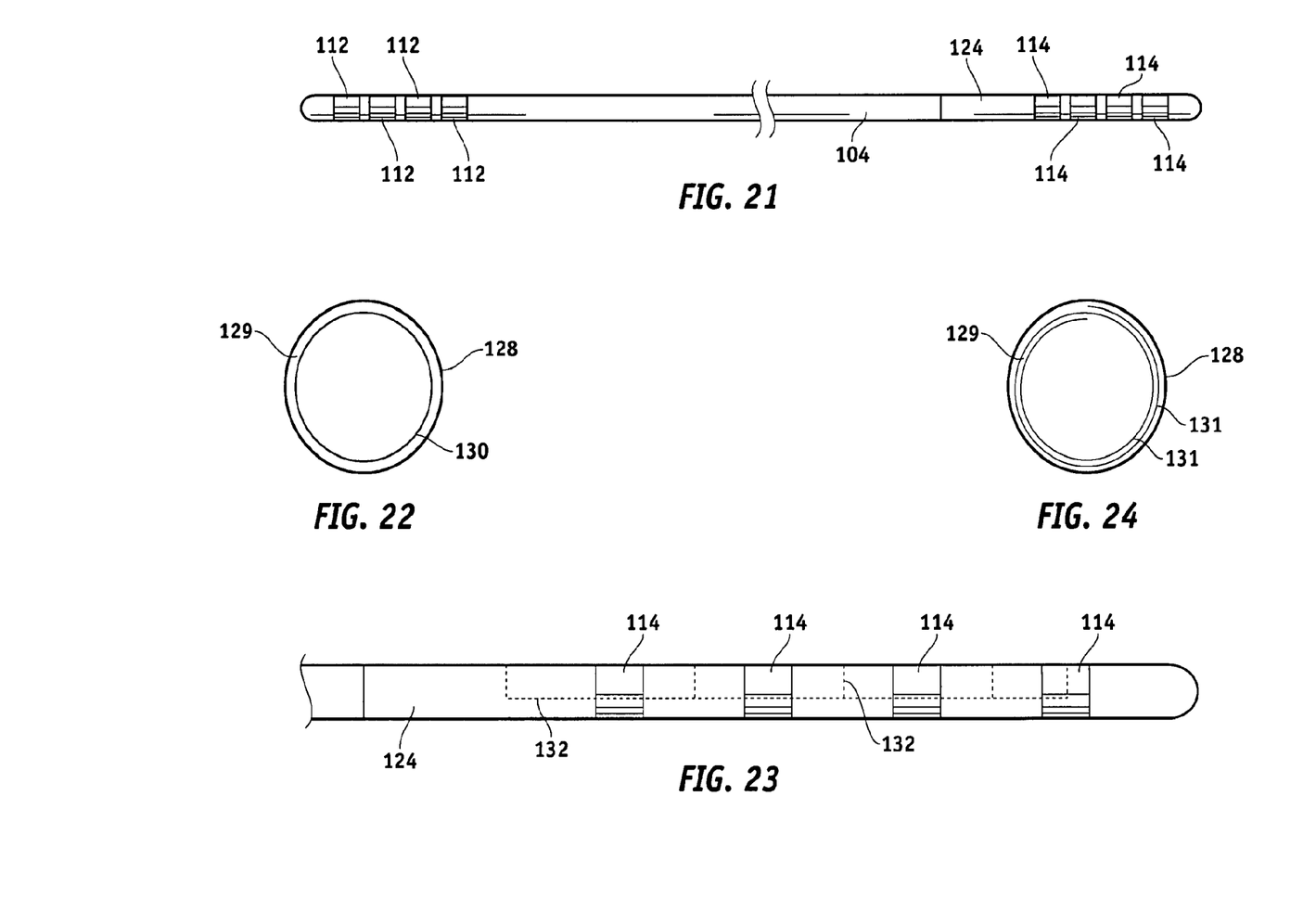
FIG. 21 is a side view of a stimulation lead utilizing a floating electrode in accordance with the present invention.
FIG. 22 is a cross-sectional view illustrating a rolled capacitor.
FIG. 23 is a side view of the distal end of a stimulation lead in accordance with an embodiment of the present invention.
FIG. 24 is a cross-sectional view of a further embodiment of a rolled capacitor.

For example, capacitive coupling between floating electrode 124 and stimulation electrodes 114 may be accomplished by configuring a capacitor within each stimulation electrode 114 (i.e. an electrode capacitor) and then electrically coupling the electrode capacitor to floating electrode 124. This may be accomplished using a rolled capacitor construction 126 shown in cross-section in FIG. 22 wherein the outer capacitor roll or plate 128 comprises the stimulation electrode and an inner roll or plate 130 comprises in inner capacitor plate. The space between the outer roll 128 and inner roll 130 may comprise a dielectric material 129 to complete the capacitor. It is then only necessary to electrically couple each of the electrode capacitors to floating electrode 124. This may be accomplished by means of a wire 132 coupled to each electrode capacitor (i.e. to one of the inner or outer plates) and to the floating electrode 124 as is shown in FIG. 23. If desired, inner roll or plate 132 may comprise multiple coils or turns 131 as shown in FIG. 24. The space between coils and plates comprises dielectric material 129.

Figures 25, 26:
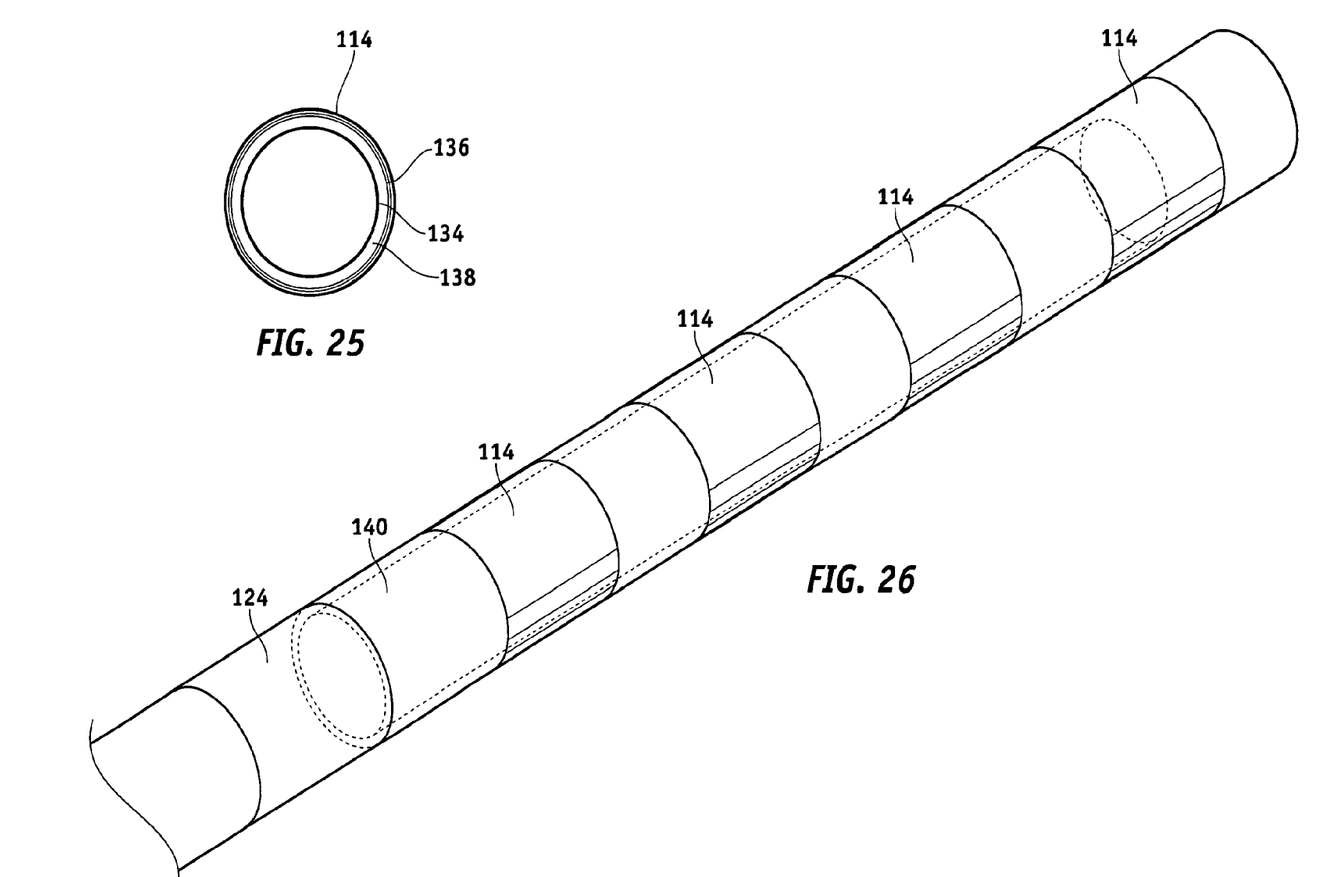
FIG. 25 is a cross-sectional view of a discoital capacitor for use in conjunction with the present invention.
FIG. 26 is an isometric view of yet another embodiment of the present invention.

Alternatively, a ceramic capacitor (e.g. a discoital capacitor) could be used to create the capacitance between floating electrode 124 and a stimulation electrode 114. Such an arrangement is shown in FIG. 25. As can be seen, a capacitor is comprised of inner and outer plates 134 and 136 separated by a ceramic material 138. This capacitor is then positioned within stimulation electrode 114 such that plate 134 is electrically coupled to electrode 114. Each of the electrode/capacitor assemblies thus formed may be electrically coupled together and to floating electrode 124 by, for example, a single wire 132 as shown in FIG. 23. Discoital capacitors are well known and further discussion is not deemed necessary; however, the interested reader is referred to U.S. Pat. No. 6,660,116 issued Dec. 9, 2003 and entitled "Capacitive Filtered Feedthrough Array for an Implantable Medical Device".

FIG. 26 illustrates yet another embodiment of the present invention. Floating contact 124 is provided with a conductive extension 140 that extends through stimulation electrodes 114 in capacitor forming relationship therewith. The area between each stimulation electrode 114 and extension 140 is occupied by a dielectric material. Thus, at high frequency (MRI frequencies), the capacitors formed by stimulation electrodes 114 and extension 140 will conduct induced current to floating electrode 124 via extension 140. This current is then dissipated into a patient's body tissue or fluid at a low current density, thus reducing unwanted heating of the stimulation electrodes 114.

While at least one exemplary embodiment has been presented in the foregoing detailed description of the invention, it should be appreciated that a vast number of variations exist. For example, while the invention has been described in connection with medical systems, the invention is equally applicable to other systems that may be adversely impacted in high frequency environments such as is encountered during an MRI scan. It should also be appreciated that the exemplary embodiment or exemplary embodiments are only examples, and are not intended to limit the scope, applicability, or configuration of the invention in any way.

The foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

What is claimed is:

1. A medical lead configured to be implanted into a patient's body, the lead comprising:
    an elongated lead body having a proximal end and a distal end;
    a conductive filer that is coupled to an electrical contact at the proximal end and that passes through an interior of the lead body to the distal end;
    a stimulation electrode coupled to said lead body at the distal end and being electrically connected to the conductive filer; and
    an electrode assembly coupled to said lead body at the distal end, said electrode assembly comprising:
        a first section comprising a ring that is electrically connected to the stimulation electrode; and
        a second section comprising a ring positioned about at least a portion of the ring of the first section and that is capacitively coupled to said first section, the second section being configured to be coupled to the patient's body.

2. A medical lead according to claim 1 wherein said second section conducts current from said stimulation electrode to the patient's body.

3. A medical lead according to claim 2 wherein said second section conducts current from said stimulation electrode at RF MRI frequencies.

4. A medical lead according to claim 1 wherein said first section and said second section have an opening therethrough for receiving said conductive filer.

5. A medical lead according to claim 1, further comprising a floating electrode electrically connected to the second section and capacitively coupled to said stimulation electrode via the capacitive coupling between the second section and the first section.

6. A medical lead according to claim 5, wherein the floating electrode is electrically coupled to the patient's body.

7. A medical lead according to claim 5, wherein the floating electrode is capacitively coupled to the patient's body.

8. A medical lead according to claim 5 further comprising a wire for electrically coupling said second section and said floating electrode.

9. A medical lead according to claim 1 wherein said second section provides substantially no conduction at stimulation frequencies.

10. A pulse stimulation system for implantation into a patient's body, the system comprising:
    a pulse generator;
    a conductive filer having a proximal end electrically coupled to said pulse generator and having a distal end;
    a lead body for housing said conductive filer;

a stimulation electrode coupled to said lead body at the distal end and being electrically connected to the conductive filer; and an electrode assembly coupled to said lead body at the distal end, said electrode assembly comprising:
- a first section comprising a ring that is electrically connected to the stimulation electrode; and
- a second section comprising a ring positioned about at least a portion of the ring of the first section and that is capacitively coupled to said first section, the second section being configured to be coupled to the patient's body.

11. A pulse stimulation system according to claim 10 wherein said second section conducts current from said stimulation electrode to the patient's body.

12. A pulse stimulation system according to claim 11 wherein said second section conducts current from said stimulation electrode at RF MRI frequencies.

13. A pulse stimulation system according to claim 10 wherein said first section and said second section have an opening therethrough for receiving said conductive filer.

14. A pulse stimulation system according to claim 10, further comprising a floating electrode electrically connected to the second section and capacitively coupled to said stimulation electrode via the capacitive coupling between the second section and the first section.

15. A pulse stimulation system according to claim 14, wherein the floating electrode is electrically coupled to the patient's body.

16. A pulse stimulation system according to claim 14, wherein the floating electrode is capacitively coupled to the patient's body.

17. A pulse stimulation system according to claim 14 further comprising a wire for electrically coupling said second section and said floating electrode.

18. A pulse stimulation system according to claim 10 wherein said second section provides substantially no conduction at stimulation frequencies.

19. A medical lead configured to be implanted into a patient's body, the lead comprising:
- an elongated lead body having a proximal end and a distal end;
- a plurality of stimulation electrodes coupled to said lead body at the distal end; and
- a plurality of electrode assemblies coupled to said lead body at the distal end, with each electrode assembly of the plurality being adjacent a corresponding stimulation electrode, each of said electrode assemblies comprising:
  - a first section comprising a ring that is electrically connected to the corresponding stimulation electrode; and
  - a second section comprising a ring positioned about at least a portion of the ring of the first section and that is capacitively coupled to said first section, the second section being configured to be coupled to the patient's body.

20. An electrode assembly for use on a lead configured to be implanted in a patient's body, the electrode assembly comprising:
- a first section comprising a ring that is configured to contact the patient's body; and
- a second section that is capacitively coupled to said first section by at least a portion of the second section being positioned within the ring and that is configured to be electrically coupled to the patient's body; wherein the second section comprises a floating electrode configured to contact the patient's body.

21. An electrode assembly according to claim 20 wherein the portion comprises at least one coil coupled in capacitor forming relationship with said first section and electrically coupled to said floating electrode.

22. An electrode assembly according to claim 21 further comprising a wire for electrically coupling said at least one coil and said floating electrode.

23. A medical lead configured to be implanted into a patient's body, the lead comprising:
- a lead body; and
- an electrode coupled to said lead body, said electrode comprising:
  - a first section comprising a ring that is configured to contact the patient's body; and
  - a second section that is capacitively coupled to said first section by at least a portion of the second section being positioned within the ring and that is configured to be electrically coupled to the patient's body; and wherein the second section comprises a floating electrode configured to contact the patient's body and is capacitively coupled to said first section via the portion being positioned within the ring.

* * * * *